(12) United States Patent
Cimino

(10) Patent No.: US 6,350,245 B1
(45) Date of Patent: Feb. 26, 2002

(54) TRANSDERMAL ULTRASONIC DEVICE AND METHOD

(76) Inventor: William W. Cimino, 578 W. Sagebrush Ct., Louisville, CO (US) 80027

( * ) Notice: Subject to any disclaimer, the term of this patent is extended or adjusted under 35 U.S.C. 154(b) by 0 days.

(21) Appl. No.: 09/219,216

(22) Filed: Dec. 22, 1998

(51) Int. Cl.$^7$ .............................................. A61B 17/22
(52) U.S. Cl. .............................................. 601/2; 601/4
(58) Field of Search .................... 601/2–4; 600/439, 600/459; 604/22

(56) References Cited

U.S. PATENT DOCUMENTS

| | | | |
|---|---|---|---|
| 4,803,995 A | 2/1989 | Ishida et al. | |
| 4,886,491 A | 12/1989 | Parisi | |
| 5,054,470 A | 10/1991 | Fry | |
| 5,209,221 A | 5/1993 | Riedlinger | |
| 5,244,458 A | 9/1993 | Takasu | |
| 5,402,792 A | 4/1995 | Kimura | |
| 5,419,761 A | 5/1995 | Narayanan | |
| 5,527,273 A | 6/1996 | Manna | |
| 5,549,544 A | 8/1996 | Young et al. | |
| 5,558,623 A | * 9/1996 | Cody | 601/2 |
| 5,665,053 A | 9/1997 | Jacobs | 601/2 |
| 5,827,204 A | 10/1998 | Grandia | |
| 5,879,314 A | * 3/1999 | Peterson et al. | 601/2 |
| 5,885,211 A | 3/1999 | Eppstein et al. | |
| 5,941,838 A | * 8/1999 | Eizenhofer | 601/2 |

OTHER PUBLICATIONS

Rod Rohrich, Separating Ultrasound–Assisted Lipoplasty Fact from Fiction Ultrasound–Assisted Lipoplasty Resource Guide, Plastic Surgery News, pp. 22–23, 1997.

* cited by examiner

*Primary Examiner*—Ruth S. Smith
(74) *Attorney, Agent, or Firm*—Merchant & Gould P.C.; Thomas H. Young

(57) ABSTRACT

In general a hand-held ultrasonic surgical apparatus with a focusing lens for fragmenting or emulsifying a predetermined volume of a medium located generally near a focal length from a concave surface of the focusing lens without significant heating of the medium includes a housing to be held and manipulated by a surgeon or physician and an acoustic assembly mounted within the housing. The acoustic assembly has a resonant vibratory frequency that is primarily determined by the length of the acoustic assembly and an axis along which the ultrasonic vibratory energy is directed. The preferred range for the resonant vibratory frequency to achieve sufficient focusing and sufficient ultrasonic power to fragment or emulsify tissue is between 100 kHz and 250 kHz. The acoustic assembly includes an ultrasonic motor, a rear driver, a front driver, a compression fastener, and a focusing lens.

6 Claims, 1 Drawing Sheet

TRANSDERMAL ULTRASONIC DEVICE AND METHOD

BACKGROUND OF THE INVENTION

This invention relates generally to surgical instruments, and, more particularly, to a surgical device for fragmentation or emulsification of soft tissues of a patient with focused delivery of ultrasonic energy.

Liposuction is a surgical procedure for altering the human form, specifically by removal of localized deposits of fat tissues that are unresponsive to diet or exercise. The procedure is also known as suction lipectomy, lipolysis, and more recently as body contour surgery, body sculpting surgery, or suction-assisted liposuction. It is most often performed by plastic surgeons, although dermatologists, gynecologists, and other surgical specialties also perform the procedure.

The liposuction procedure is typically accomplished by inserting a small liposuction cannula through an incision in the skin, applying a suction source to the end of the liposuction cannula that remains outside of the body, and forcing the working end of the liposuction cannula forward and backward in the layer of fatty tissue. The fatty tissue is torn, crushed, or avulsed, and is then aspirated through small openings along the sides of the liposuction cannula near the tip and then through a central lumen in the liposuction cannula to a tissue canister placed in-line with the liposuction cannula and the suction source. The procedure may involve multiple incisions and many passes of the liposuction cannula in each incision to achieve the desired cosmetic effect for the patient.

The liposuction procedure can be traumatic for the patient. The liposuction cannula does not discriminate between adipose tissue and other tissues such as nerves, blood vessels, or lymph tissues. The mechanical disruption of the above-named tissues by the liposuction cannula may result in, among other things, bleeding, bruising, temporary numbness, or swelling. Further, the final cosmetic result achieved for the patient is a function of the skill of the surgeon, the patient, and the type of surgical instrumentation used in the surgery. Liposuction cannulae used in the liposuction procedure may remove more adipose tissue from one area than another area in the patient, resulting in skin contour irregularities and a final cosmetic result for the patient that is not smooth or uniform.

Therefore, there is a need to improve the surgical instrumentation for the liposuction procedure to help the surgeon to better discriminate between adipose tissue and other tissues such as nerves, blood vessels, and lymph tissues, so that the adipose tissues can be fragmented and removed while the remaining tissues are damaged as little as possible or not at all. Further, there is a need to improve the surgical instrumentation for the liposuction procedure so that adipose tissue is removed in a more uniform and predictable manner so that an improved cosmetic result is achieved for the patient.

Recently, several instruments have combined ultrasonic vibrations and the liposuction cannula to improve upon the tissue discrimination capability of the liposuction cannula and to provide an instrument that removes adipose tissue more uniformly than current liposuction cannulae. This procedure is commonly referred to as ultrasound-assisted lipoplasty. In a typical ultrasound-assisted lipoplasty procedure, an ultrasonically vibrating cannula is inserted through an incision in the patient's skin and passed forward and backward through the adipose tissue layer, directly contacting the tissues to be treated. The ultrasonically vibrating cannula fragments or emulsifies the adipose tissues, which are then usually aspirated through a central lumen in the ultrasonically vibrating cannula.

Initial experiences with the ultrasound-assisted lipoplasty procedure have been mixed. A comparison of the suction-assisted liposuction and ultrasound-assisted lipoplasty approaches with currently available surgical instruments for both procedures was recently given in Ultrasound-Assisted Assisted Lipoplasty Resource Guide, published in Plastic-Surgery News, a publication of The American Society of Plastic and Reconstructive Surgeons, 1997. In the article the author cites the disadvantages of the current ultrasound-assisted lipoplasty procedure compared to the suction-assisted liposuction procedure as: 1) burns of the skin are possible, 2) longer incisions are needed, 3) seromas are more common, 4) longer operating times are required, and 5) greater expenses are incurred. Thus, current ultrasound-assisted lipoplasty surgical systems that use an ultrasonically vibrating cannula for fragmentation and aspiration of adipose tissues are more costly and slower than the suction-assisted liposuction procedure and have the potential to damage tissues beyond that of suction-assisted liposuction, including burns of the skin and seroma formation. There is, therefore, a need to increase the speed of the ultrasound-assisted lipoplasty procedure and to minimize the potential for burns or seroma formation.

The use of focused ultrasound has long been known, specifically for diagnostic imaging purposes where the ability to focus the ultrasonic beam determines the imaging resolution of the system. Diagnostic imaging systems operate at frequencies between 1 MHz and 20 MHz to achieve the desired imaging resolution. The ultrasonic power coupled to the tissue of the patient is kept to a minimum to prevent damage to the skin layer and the deeper tissues.

The ability to focus an ultrasonic beam is related to the wavelength of the selected frequency in tissue. At 20 kHz the wavelength in tissue is approximately 7.5 centimeters, fundamentally limiting the ability to focus the beam to a minimum diameter of about 7.5 centimeters, generally too large for a surgical application of ultrasonic energy where the intent is to destroy or fragment a much smaller and precisely controlled volume of tissue in a patient. At 1 MHz the wavelength in tissue is approximately 0.15 centimeters, representing about the limit of resolution at this frequency. While it is possible to achieve sufficient focusing capability at the higher ultrasonic frequencies, such as 1 MHz, the majority of ultrasonic power at the higher frequencies is absorbed in the tissue in the form of heat, creating unsatisfactory thermal injury to tissues if the power density is large enough. Thus, there is a need to provide an instrument that can focus ultrasonic energy at the lower ultrasonic frequencies while supplying sufficient ultrasonic power so that the desired tissue fragmentation is obtained without significant heating of the tissues of the patient.

The most common method of generating ultrasonic energy for surgical or diagnostic applications is with piezoelectric ceramic materials formed to make a piezoelectric transducer that converts electrical energy to vibratory motion. In most applications the piezoelectric transducer is bonded to a flat applicator or an acoustic lens and is driven at the resonant vibratory frequency of the piezoelectric transducer that is determined primarily by the thickness of the piezoelectric transducer. The thickness of a piezoelectric transducer may range from a few tenths of a millimeter to several millimeters. The fundamental equation relating the resonant vibratory frequency and the transducer thickness for a ½ wave free resonance is $f=c/2l$ where $f$ is the frequency in Hz, c is the wave speed of the piezoelectric ceramic material in centimeters per second, and l is the thickness of the piezoelectric transducer in centimeters. A 0.35 centimeter thick piezoelectric transducer vibrating in the thickness mode has a ½ wave free resonance of approximately 417 kHz. At 25 kHz the thickness becomes approximately 5.8 centimeters. Thus, it is difficult to create low frequency transducers using this approach because the thickness of the piezoelectric transducer becomes prohibitive.

Piezoelectric ceramic materials have physical properties that fundamentally limit their ability to convert electrical energy to vibratory motion. There are limitations for voltage, current, temperature, and mechanical stress, most notably tensile stress. As the piezoelectric transducer expands in response to an electrical driving signal the piezoelectric ceramic material enters a state of tensile stress. Ceramic materials of any type are generally not able to withstand significant tensile stress. Thus, the amount of ultrasonic vibratory power that can be obtained from a piezoelectric transducer is limited by a maximum amount of tensile stress sustainable by the piezoelectric ceramic material used to fabricate the piezoelectric transducer.

Many patents disclose improvements and solutions for ultrasound-assisted lipoplasty instruments for removal of adipose tissue from the human body. U.S. Pat. No. 4,886,491 to Parisi has a method of removing fatty tissue from a patient using an ultrasonic probe and its direct percutaneous energy application to thermally melt at least some of the fatty tissue. U.S. Pat. No. 5,244,458 to Takasu has an ultrasonic handpiece with a hollow cannula with a plurality of suction openings. U.S. Pat. No. 5,419,761 to Narayanan has an ultrasonic handpiece with a rigid tube with an axially extending lumen for suction. U.S. Pat. No. 5,527,273 to Manna has an ultrasonic lipectomy probe with an enlarged head on the distal end and a longitudinally extending channel in the probe for suction. All of the aforementioned inventions utilize ultrasonic probes that are passed through the skin and directly contact and destroy the tissue to be treated.

Many patents disclose improvements and solutions for the non-invasive use of ultrasound to heat tissues of a patient or to create cavitation within the tissues of a patient. U.S. Pat. No. 5,827,204 to Grandia has an ultrasonic transducer that includes a low frequency ultrasonic signal and a second higher frequency ultrasonic signal, the combination for creating vaporous cavitation within tissues. This invention applies ultrasonic energy to the surface of a patient with the ultrasonic energy focused at a distance below the surface and coupled to the patient through a coupling medium, presumably a fluid, as shown in FIG. 1 of the disclosure. As such, the transducer face, which has the lowest ultrasonic energy intensity in a focused system, does not contact the patient. In this invention the resonant vibratory frequency of the device is determined by the thickness and shape of the ultrasonic transducer. The method or technique by which the low frequency ultrasonic vibratory energy is generated is not disclosed. This invention does not include any means to limit the tensile stresses generated in the piezoelectric transducer. U.S. Pat. No. 5,054,470 to Fry has a focused ultrasound beam with a fluid coupling medium between a piezoelectric transducer and an acoustic lens and an air pressure means contacting the rear surface of the piezoelectric transducer. In this invention the resonant vibratory frequency is determined by the thickness and shape of the flat piezoelectric transducer plate. This invention does not include any means to limit the tensile stresses generated in the piezoelectric transducer. U.S. Pat. No. 5,402,792 to Kimura has an ultrasonic transducer and wave-emitting surface with multiple concave surface elements so that multiple focal points are obtained. In this invention the resonant vibratory frequency is determined by the thickness and shape of the elongated rectangular planar transducer. This invention does not include any means to limit the tensile stresses generated in the piezoelectric transducer. U.S. Pat. No. 5,209,221 to Riedlinger has an ultrasonic carrier frequency and an ultrasonic pulse generating means that radiates pulsed ultrasonic energy toward a focusing surface that reflects the pulsed ultrasonic energy toward a target. None of these patents disclose a means to generate and focus low frequency ultrasonic energy with sufficient power to fragment tissues of a patient using a single resonant vibratory frequency.

While some of the patented devices may disclose and claim improvements and solutions to ultrasound-assisted lipoplasty instruments or focused ultrasound systems for tissue lesioning or the production of cavitation, none address or appreciate the needs and design considerations discussed above for effective and expedient soft tissue fragmentation or emulsification without significant heating of the tissues. Specifically, none of disclosed inventions utilize a direct application of ultrasonic energy to the skin of a patient to fragment or emulsify soft tissues of the body at a desired depth from the skin using a focusing lens and operating at a single resonant vibratory frequency.

OBJECTS OF THE INVENTION

It is, among other desirable attributes, a general object of the present invention to provide an improved ultrasonic surgical apparatus for fragmentation or emulsification of soft tissues in a patient.

It is a further object of the present invention to provide an improved ultrasonic surgical apparatus for fragmentation or emulsification of soft tissues in a patient which maximizes the fragmentation or emulsification of adipose tissues and minimizes trauma to other tissues such as nerves, blood vessels, and lymph tissues, and thus decreases healing time, decreases patient pain, reduces swelling, and decreases bleeding.

It is still a further object of the present invention to provide an improved ultrasonic surgical apparatus for fragmentation or emulsification of soft tissues in the patient that increases the speed of the fragmentation or emulsification process and thereby reduces the time required to complete the surgical procedure.

It is yet still a further object of the present invention to provide an improved ultrasonic surgical apparatus that provides uniform, controllable, and predictable fragmentation or emulsification of soft tissues in a patient and which therefore yields an improved cosmetic result for the patient.

It is a specific object of the present invention to provide an improved ultrasonic surgical apparatus for fragmentation or emulsification of soft tissues of a patient where the ultrasonic energy is applied to the skin of the patient with a focusing lens for fragmenting or emulsifying soft tissues near a focal length below the skin without significant heating of the tissues of the patient using a single resonant vibratory frequency determined by an acoustic assembly of the ultrasonic surgical apparatus.

SUMMARY OF THE INVENTION

In general a hand-held ultrasonic surgical apparatus with a focusing lens for fragmenting or emulsifying a predetermined volume of a medium located generally near a focal length from a concave surface of the focusing lens without significant heating of the medium includes a housing to be held and manipulated by a surgeon or physician and an acoustic assembly mounted within the housing. The acoustic assembly has a resonant vibratory frequency that is primarily determined by the length of the acoustic assembly and an axis along which the ultrasonic vibratory energy is directed. The preferred resonant vibratory frequencies to achieve sufficient focusing and sufficient ultrasonic power to fragment or emulsify tissue is a low frequency range between 100 kHz and 250 kHz. The acoustic assembly includes an ultrasonic motor, a rear driver, a front driver, a compression fastener, and a focusing lens. The ultrasonic motor has a distal surface and a proximal surface and is aligned along the axis. The preferred material for the ultrasonic motor is a piezoelectric ceramic such as PZT-8 or PZT-4. The rear driver is connected to the proximal surface of the ultrasonic motor and aligned along the axis. The front driver is connected to the distal surface of the ultrasonic motor and aligned along the axis. The compression fastener passes through the rear driver and the ultrasonic motor and connects to the front driver so that the ultrasonic motor is under compression between the front driver and the rear driver providing compressive forces to the piezoelectric ceramic elements of the ultrasonic motor. Sufficient compression of the ultrasonic motor is provided by the compression fastener so that there are no tensile stresses experienced by the ultrasonic motor during the expansion phase of a vibratory cycle. The focusing lens is connected to the front driver and aligned along the axis for application to the skin of a patient. The focusing lens may be fabricated from the same material as the front driver and may be integral or contiguous therewith. The focusing lens has generally concave surface for radiating ultrasonic vibratory energy toward a predetermined volume within the tissues of a patient located generally near the focal length from the concave surface. The predetermined volume is generally defined by the ultrasonic energy beam pattern near the focal length from the concave surface of the focusing lens. The ultrasonic vibratory energy is spread over the concave surface of the focusing lens and radiates from the concave surface so that the ultrasonic vibratory energy is concentrated within the predetermined volume located generally near the focal length from the concave surface. This concentration of energy allows relatively low power densities to exist on the concave surface of the focusing lens so that the skin of the patient is not damaged. The concentrated energy and consequentially higher power densities exist within the predetermined volume within the tissues of the patient where tissue fragmentation or emulsification is to occur.

The concave surface of the focusing lens may have a constant radius of curvature or alternatively the curvature may be parabolic or elliptical. The preferred curvature is a constant radius of curvature.

The focusing lens may have suction ports. The suction ports may be connected to suction to draw the skin of a patient into the focusing lens so that improved coupling of the ultrasonic vibratory energy to the skin of the patient is obtained.

Also claimed is a method of fragmenting or emulsifying a medium near a focal length from a surface of a focusing lens, the method having the steps of: generating ultrasonic vibratory energy on a concave surface of a focusing lens; applying the focusing lens to the medium; concentrating the generated ultrasonic vibratory energy in a predetermined volume within the medium near a focal length from the concave surface of the focusing lens, and fragmenting or emulsifying the medium within the predetermined volume at the focal length from the concave surface of the focusing lens:

BRIEF DESCRIPTION OF THE DRAWINGS

The novel features of the invention to be protected are set forth in the appended claims. The invention will be best understood by reference to the following figure when read in conjunction with the detailed description of the invention.

DETAILED DESCRIPTION OF THE INVENTION

Figure 1:
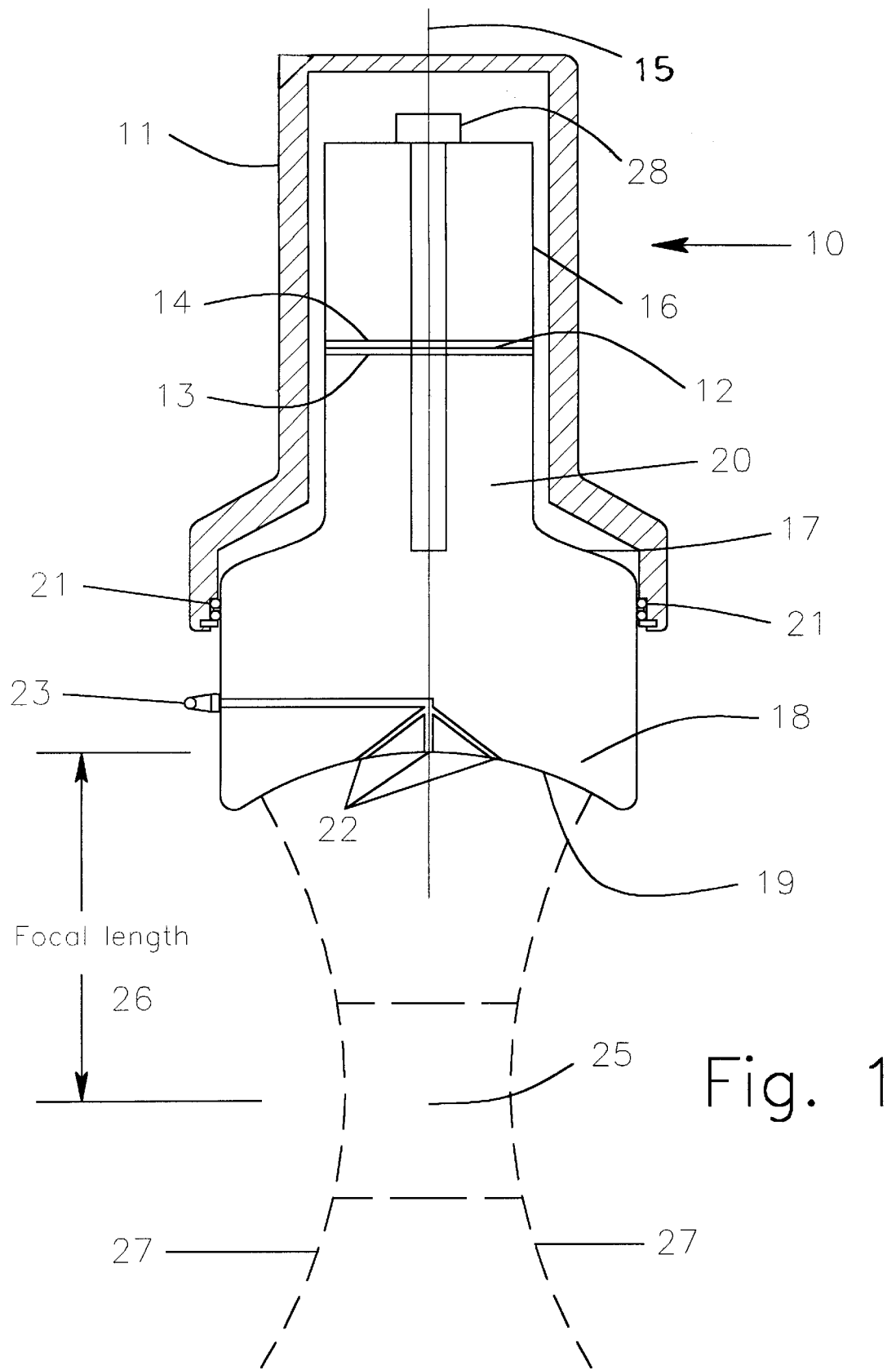
FIG. 1 is a partial schematic diagram generally in cross-section of the improved ultrasonic surgical apparatus with a focusing lens used to deliver concentrated ultrasonic energy near a focal length within a medium.

A partial schematic diagram of the improved ultrasonic surgical apparatus 10 is shown in FIG. 1. The ultrasonic surgical apparatus 10 has a housing 11 to be held and manipulated by the surgeon. The preferred material for the housing is a polymer such as Delrin (acetal homopolymer) or Radel (polyphenylsulfone). Metallic materials such as aluminum or stainless steel could also be used. An acoustic assembly 20 is mounted within the housing 11. The preferred method of mounting is to use polymeric O-rings 21 to suspend the acoustic assembly 20 within the-housing 11. The acoustic assembly 20 has an axis 15 along which the ultrasonic vibratory energy is directed, The acoustic assembly 20 has a resonant vibratory frequency that is determined primarily by a length of the acoustic assembly, the length of the acoustic assembly measured along the axis 15. The resonant vibratory frequency may be in the range from 50 kHz to 500 kHz, preferably between 100 kHz and 250 kHz. The acoustic assembly 20 has an ultrasonic motor 12 with a distal surface 13 and a proximal surface 14, the ultrasonic motor 12 aligned along the axis 15. The preferred material for the ultrasonic motor 12 is a piezoelectric ceramic such as PZT-4 or PZT-8. The ultrasonic motor 12 receives electrical power and converts the electrical power to ultrasonic vibratory energy at the frequency determined by the acoustic assembly 20. The acoustic assembly 20 has a rear driver 16 connected to the proximal surface 14 of the ultrasonic motor 12, the rear driver aligned along the axis 15. The preferred materials for the rear driver are aluminum or titanium. The acoustic assembly 20 has a front driver 17. connected to the distal surface 13 of the ultrasonic motor 12, the front driver 17 aligned along the axis 15. The preferred materials for the front driver are aluminum or titanium. The acoustic assembly 20 has a compression fastener 28 aligned along the axis 15 and passing through the rear driver 16 and the ultrasonic motor 12 and connected to the front driver 17 so that the ultrasonic motor 12 is under compression between the front driver 17 and the rear driver 16. The preferred type of compression fastener 28 is a threaded bolt with female threads in the front driver 17. The acoustic assembly 20 has a focusing lens 18 connected to the front driver 17 and aligned with the axis 15 for delivering ultrasonic vibratory energy to a medium. The focusing lens 18 has a generally concave surface 19 for radiating ultrasonic vibratory energy toward a predetermined volume 25 within the medium located generally near a focal length 26 from the concave surface 19. The dashed lines in FIG. 1 extending from the concave surface 19 indicate an ultrasonic vibratory energy beam profile with a focal length 26 and the concentration of the ultrasonic vibratory energy within a predetermined volume 25. The preferred shape of the concave surface 19 of the focusing lens 18 is a curvature with a constant radius. The following formula may be used to estimate a desired focal length: $L_f=R/(1-C_m/C1)$ where $L_f$ is the focal length in centimeters, R is the radius of curvature in centimeters, $C_m$ is the wave speed of the medium in centimeters per second, and C1 is the wave speed of the material of the focusing lens in centimeters per second. For example, an aluminum lens radiating into water with a focal length of 6.0 centimeters will have a radius of curvature of approximately 4.2 centimeters.

Other curvatures such as elliptical or parabolic shaped surfaces may also be used. The preferred materials for the focusing lens 18 are aluminum or titanium. The focusing lens 18 may be fabricated from the same piece of material as the front driver 17. Polymeric materials such as polystyrene may be used but must be bonded to the front driver 17.

In a further refinement the focusing lens 18 may have suction ports 22 to draw the skin of a patient into the focusing lens 18 to improve the coupling of the ultrasonic vibratory energy to the patient. Three suction ports 22 are shown in FIG. 1. The suction ports 22 are connected to suction (not shown in FIG. 1) using a tubing barb 23.

What is claimed is:

1. A hand-held ultrasonic surgical apparatus for fragmenting or emulsifying a predetermined volume of animal tissue located beneath the skin of an animal comprising:

a housing to be held and manipulated during surgery;

an acoustic assembly mounted within the housing that vibrates at a resonant vibratory frequency, the resonant vibratory frequency determined by the length and shape of the acoustic assembly and within the range between 100 kHZ and 250 kHZ;

the acoustic assembly having an axis along which ultrasonic vibratory energy is directed and an ultrasonic motor with a distal surface and a proximal surface, the ultrasonic motor aligned along the axis;

a rear driver of the acoustic assembly connected to the proximal surface of the ultrasonic motor and aligned along the axis;

a front driver of the acoustic assembly connected to the distal surface of the ultrasonic motor and aligned along the axis;

a compression fastener aligned along the axis and passing through the rear driver and the ultrasonic motor and connected to the front driver so that the ultrasonic motor is under compression between the front driver and the rear driver; and a focusing lens connected to the front driver within the acoustic assembly and aligned along the axis thereof, said focusing lens having a generally concave surface for contact with the skin of the animal and cooperating with the acoustic assembly to deliver vibratory energy to the animal tissue, concentrated generally at a focal length from the concave surface, without significant heating of the animal tissue.

2. The hand-held ultrasonic surgical apparatus of claim 1 wherein at least part of the concave surface of the focusing lens has a constant radius of curvature.

3. The hand-held ultrasonic surgical apparatus of claim 1 wherein the focusing lens is generally metallic.

4. The hand-held ultrasonic surgical apparatus of claim 1 wherein the focusing lens is generally polymeric.

5. The hand-held ultrasonic surgical apparatus of claim 1 wherein the focusing lens and the front driver comprise a single piece of material.

6. The hand-held ultrasonic surgical apparatus of claim 1 further comprising:

a source of suction and suction ports associated with the focusing lens and connected to the source of suction to draw the skin into the focusing lens for improved coupling of the ultrasonic vibratory energy with the animal tissue.

* * * * *